United States Patent [19]

Schroeppel

[11] Patent Number: 4,766,902
[45] Date of Patent: Aug. 30, 1988

[54] AUTOMATIC SENSITIVITY CONTROL FOR CARDIAC PACER

[75] Inventor: Edward A. Schroeppel, Miramar, Fla.

[73] Assignee: Telectronics N.V., Netherlands Antilles

[21] Appl. No.: 870,398

[22] Filed: Jun. 4, 1986

[51] Int. Cl.⁴ .............................................. A61N 1/36
[52] U.S. Cl. ......................... 128/419 PG; 128/419 P
[58] Field of Search ............... 128/419 PT, 419 PG, 128/696, 708

[56] References Cited

U.S. PATENT DOCUMENTS

| 4,240,442 | 12/1980 | Andresen et al. | 128/708 |
| 4,325,384 | 4/1982 | Blaser et al. | 128/696 |
| 4,513,752 | 4/1985 | Weyant | 128/696 |
| 4,585,001 | 4/1986 | Belt | 128/708 |
| 4,677,986 | 7/1987 | DeCote, Jr. | 128/697 |

Primary Examiner—William E. Kamm
Assistant Examiner—Timothy J. Keegan
Attorney, Agent, or Firm—George H. Gerstman

[57] ABSTRACT

A cardiac pacer is provided which includes a pulse generator for providing pacing pulses and an electrical lead for connection to a chamber of the heart. A pair of separate sensing amplifiers sense selected activity of the heart chamber. One of the sensing amplifiers has a slightly lower threshold and thus a slightly higher sensitivity level than the other sensing amplifier. The thresholds of the respective sensing amplifiers are automatically adjusted so that the first sensing amplifier will sense the selected activity of the heart chamber and the other sensing amplifier will not sense the selected activity.

8 Claims, 3 Drawing Sheets

AUTOMATIC SENSITIVITY CONTROL FOR CARDIAC PACER

CROSS-REFERENCE TO RELATED APPLICATIONS

This application is related to application Ser. No. 874,444, filed June 16, 1986, and application Ser. No. 884,014, filed July 10, 1986.

FIELD OF THE INVENTION

This invention concerns a novel automatic sensitivity control for cardiac pacers.

BACKGROUND OF THE INVENTION

Cardiac pacing system include a cardiac pacer connected to a lead which conducts stimuli from the pacer to an electrode implanted either on the surface of or within the cardiac chambers. Certain cardiac pacers, including those designated VOO pacers, emit stimuli at a certain predetermined rate, in pulses per minute. However, there are certain other models, including those designated VVI pacers, in which the output pulse is suppressed or ineffective in the presence of naturally occurring cardiac electrical activity. Such models detect cardiac electrical activity via the lead during a part of or a portion of the interval termed the alert period between output pulses. When such activity is detected or is of sufficient magnitude to be detected during the appropriate portion of the pulse to pulse interval, a new timing cycle is initiated, with time zero of the new interval being the time of detection of the electrical activity. Such electrical activity detected in, e.g., the ventricle, may be that which normally occurs from the atrium to the ventricle or may be a premature ventricular or atrial contraction dependent upon the lead placement and pacer type.

Such cardiac pacers which detect electrical activity during the alert period must have a sensitivity enabling such detection. The sensitivity of a cardiac pacer is generally considered to be that level, in millivolts, which the electrical activity resulting from the depolarization of the cardiac muscle must exceed within a given time period for the cardiac depolarization to be detected by the sensing amplifier of the cardiac pacer. For example, if the sensitivity of a cardiac pacer has been set at one millivolt, then the cardiac electrical depolarization must obtain the one millivolt level within, for example, a 30 milliseconds time period to be detected by the cardiac pacer, thereby suppressing or rendering ineffective the output stimulus and resetting the timing cycle of the cardiac pacer.

The sensitivity of these "sensing" cardiac pacers may be preset during manufacture. In other models of sensing cardiac pacers, the sensitivity may be externally programmed to various levels. Such externally programmed changes in sensitivity are accomplished by the use of an external device and usually require a visit to the physician's office. Therefore, there is no automatic change in sensitivity levels if spontaneous electrical activity is not detected by the implanted cardiac pacer. Also, there is no change in sensitivity in those situations in which the sensitivity is below that needed to detect the electrical activity of a spontaneous depolarization.

The importance of proper sensitivity adjustment cannot be overemphasized. If the sense amplifier of the pacer is not sensitive enough, proper sensing will not occur. On the other hand, if the sense amplifier is too sensitive, it may sense noise and myopotentials. Although a physician may be able to maintain proper sensitivity of the pacer, many patients are unable to see their physicians often. Thus although the sense amplifier of a pacer is programmed correctly at a particular time, the parameters may change at a subsequent period of time and the sensitivity of the sense amplifier may be either too low or too high.

Therefore, it is an object of the present invention to provide a cardiac pacer in which sensitivity is automatically adjusted to sense spontaneous cardiac electrical activity.

Other objects and advantages of the present invention will become apparent as the description proceeds.

SUMMARY OF THE INVENTION

In accordance with the present invention, a cardiac pacer is provided which includes a pulse generator for providing pacing pulses, and an electrical lead is provided for connection to a chamber of the heart. The improvement comprises a pair of separate sensing amplifiers for sensing selected activity of the heart chamber. The electrical lead is connected to both of the separate sensing amplifiers. One of the sensing amplifiers has a slightly lower threshold and thus a slightly higher sensitivity level than the other sensing amplifier. The thresholds of the respective sensing amplifiers are adjusted so hat the first sensing amplifier will sense the selected activity of the heart chamber and the other sensing amplifier will not sense the selected activity of the heart chamber.

In the illustrative embodiment, the thresholds of the respective sense amplifiers are maintained to provide the situation in which the first sense amplifier senses while the second sense amplifier does not sense, by constantly readjusting their sensitivity. If, during a sensing interval, both sense amplifiers sense, the sensitivity is too high making the pacer susceptible to noise, crosstalk and myopotential sensing. Thus the sensitivities of both sense amplifiers are readjusted to a next lower value.

On the other hand, if neither of the sense amplifiers senses during a sense interval, the sensitivities of the sense amplifiers are readjusted to the next higher value. However, prior to making an adjustment it is preferred that several intervals be examined since no cardiac activity may, in fact, exist to be sensed.

The cardiac pacer of the present invention may be single or dual chamber, unipolar or bipolar, and in accordance with the present invention the sense amplifiers may be programmable by the user to override the automatic feature when desired.

A more detailed explanation is provided in the following description and claims, and is illustrated in the accompanying drawings.

DETAILED DESCRIPTION OF THE ILLUSTRATIVE EMBODIMENT

Figure 1:
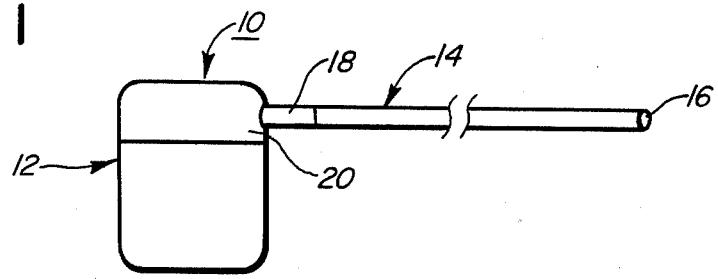
FIG. 1 is an elevational view of a cardiac pacing system in accordance with the present invention.

Referring to FIG. 1, there is shown an implantable cardiac pacing system 10 comprising a microprocessor-based pacer 12 and its pervenous lead 14. The lead 14 has at its distal end an electrode 16 which is bonded to a helically coiled conductor wire. At the proximal end of the lead 14, the conductor wire is bonded to a lead terminal assembly 18 which is contained within the neck 20 of the implantable cardiac pacer 12. The lead terminal assembly 18 is in contact with the circuitry contained within the implantable cardiac pacer. The helically coiled conductor wires are contained within an insulating sheath generally of silastic or polyurethane.

Although the description pertains to a unipolar lead and a ventricular demand pacer, the circuitry and operation described herein can be utilized in a dual chambered pacer, an atrial sensing pacer or a ventricular sensing pacer with either the unipolar or bipolar lead configuration.

Figure 2A:
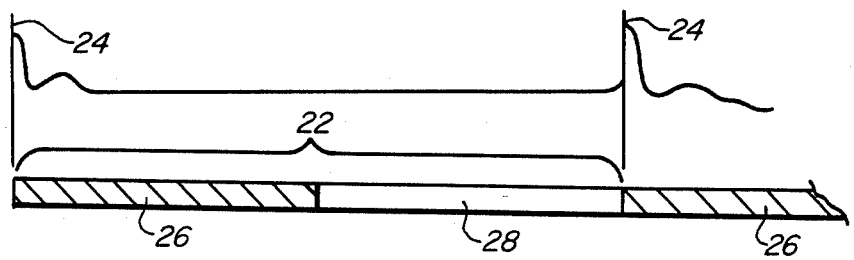
FIG. 2A is a diagram of a timing cycle occurring during stimulation.
Figure 2B:
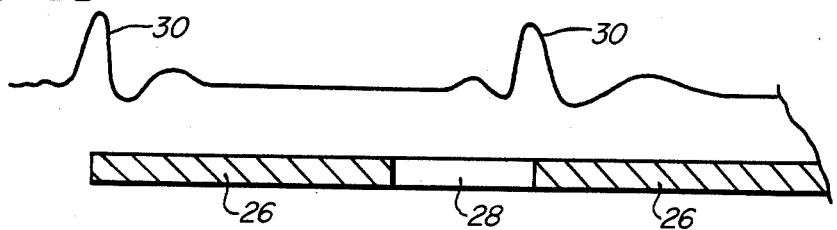
FIG. 2B is a diagram of the timing cycle of FIG. 2A that has been reset by naturally occurring ventricular activity.

Referring to FIGS. 2A and 2B, ventricular demand pacer 12 is designed so that the interval between two stimuli 24 is divided into two periods, a refractory period 26 and an alert period 28. Either the emission of a stimulus 24 (FIG. 2A) or detection of spontaneous electrical activity 30 (FIG. 2B) initiates a refractory period 26. Detection of spontaneous electrical activity 30 terminates the alert period 28 (FIG. 2B).

The stimulus 24 is transmitted from the implantable cardiac pacer 12 to the ventricle via the helical conductor wire within the insulation of the lead 14 through the distal electrode 16. Similarly, spontaneous ventricular electrical activity falling within the alert period 28 of the pulse to pulse interval 22 is sensed via the distal electrode 16 and transmitted to the ventricular sensing cardiac pacer 12.

Figure 3:
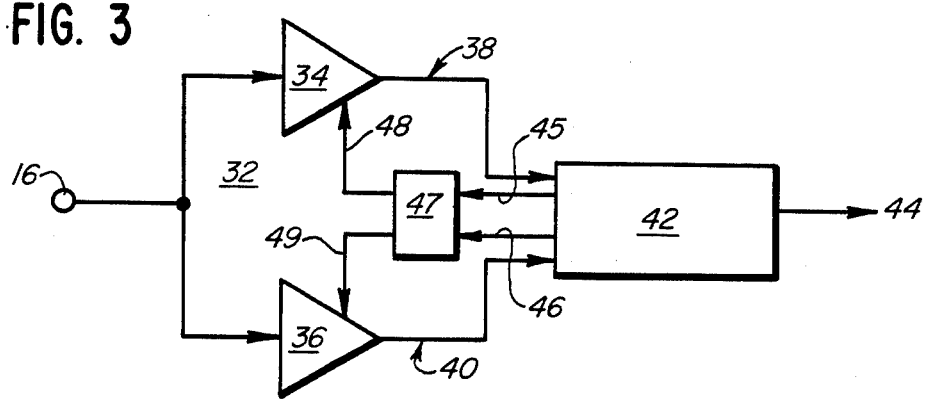
FIG. 3 is a block diagram of a sensing circuit used in the cardiac pacing system of the present invention.

Referring to FIG. 3, within the cardiac pacer is a sensing circuit 32 comprising two sensing amplifiers 34, 36. The output 38, 40 of the amplifiers 34, 36 serves as the input to a controller 42 or a portion of a microprocessor controlling electrical activity sensing. The atrial and ventricular channels of a dual chambered pacer would have two such amplifiers per channel. The controller 42 outputs a signal via line 44, indicating that sensing of a spontaneous electrical event 30 has occurred, to the timing/pacing circuit to reset the timing cycle. Absence of the signal on line 44 would indicate lack of spontaneous electrical activity, causing the timing cycle to run its course. At the end of the alert period 28, a stimulus 24 would issue.

Additionally, the controller 42 also outputs an "increase sensitivity" signal via line 45 and a "decrease sensitivity" signal via line 46 to a sensitivity adjustment circuit 47 to adjust the threshold of each of the sensing amplifiers 34, 36 via lines 48 and 49, respectively. These amplifiers 34, 36 are preferably identical and the threshold of each can be set individually. The sensitivity adjustment circuit 47 may be a conventional voltage or current divider circuit under the control of commands from the pacer's microprocessor.

The threshold of the sensing amplifier is that level of input signal which is detected. Any signal below this level is not detected. For example, if the threshold of the sensing amplifier is one millivolt, then any electrical activity of one millivolt and above with the frequency components matching the frequency response of the sensing amplifier will be detected. Further, the threshold of amplifier 34 is always slightly lower than that of amplifier 36. The ideal situation or the ideal setting of the threshold of the sensing amplifiers is that in which sensing amplifier 34 detects spontaneous electrical activity and sensing amplifier 36 does not.

The thresholds of the amplifiers 34, 36 are not reset or changed with each detected electrical event. Some predetermined or programmed number of events must be detected before the threshold is reset. For illustrative purposes, this number is four, although other numbers may be used.

Figure 4:
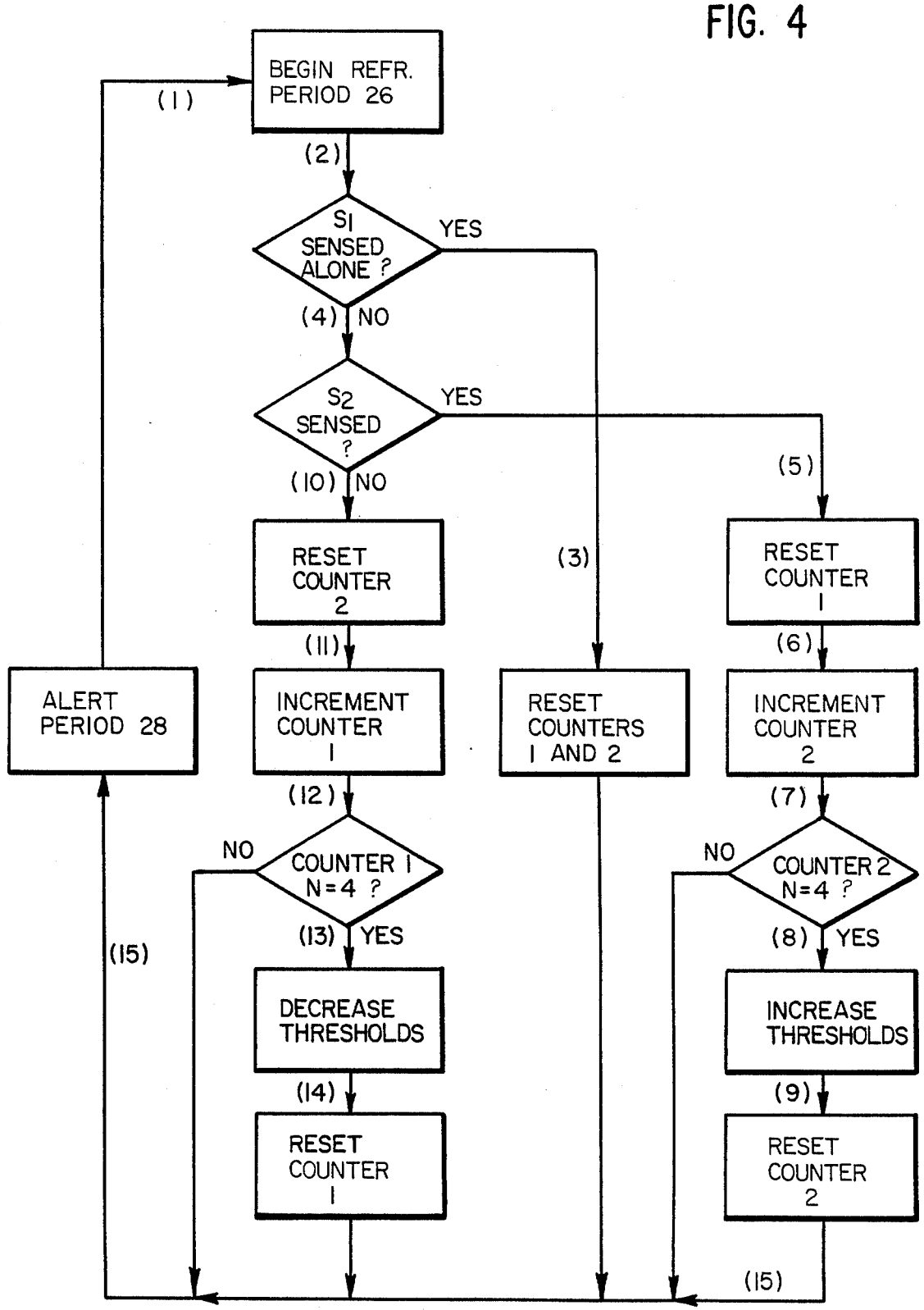
FIG. 4 is a flow chart of the cardiac pacing system of the present invention.

The operation of the amplifiers is illustrated in the flow chart of FIG. 4, in which S1 is the output signal from amplifier 34 and S2 is the output signal from amplifier 36. The flow chart of FIG. 4 eliminates details of pacer timing, noise windows, counter initialization, etc., and it assumes steady state operation. Referring to FIG. 4:

Step 1: Refractory period 26 begins. Occurrence of sensed events during previous alert period 28 has been stored.

Step 2: During the previous alert period 28 has sense amp 34 sensed and sense amp 36 not sensed? If yes, to to step 3. If not, go to step 4.

Step 3: Ideal sensing has just occurred. Reset both counters and proceed to next alert period (step 15) in accordance with pacer timing.

Step 4: Has sense amp 36 sensed? If yes, sensitivity is potentially too high. Go to step 5. If no, then neither sense amp has sensed. Sensitivity is potentially too low. Go to step 10.

Step 5: Reset counter 1. Go to step 6.

Step 6: Increment counter 2. Go to step 7.

Step 7: Has count in counter 2 reached programmable value N=4? If not, go to step 15. If yes, go to step 8.

Step 8: Decrease both sensitivities one step. Go to step 9.

Step 9: Reset counter 2 count to zero. Go to step 15.

Step 10: Neither sense amp has sensed. Sensitivity is potentially too low. Reset counter 2. Go to step 11.

Step 11: Increment counter 1. Go to step 12.

Step 12: Has count in counter 1 reached programmable value N=4? If not, go to step 15. If yes, go to step 13.

Step 13: Increase both sensitivities one step. Go to step 14.

Step 14: Reset counter 1 count to zero. Go to step 15.

Step 15: In accordance with pacer timing, proceed into alert period. Store sensed events. Go to step 1.

Figure 5:
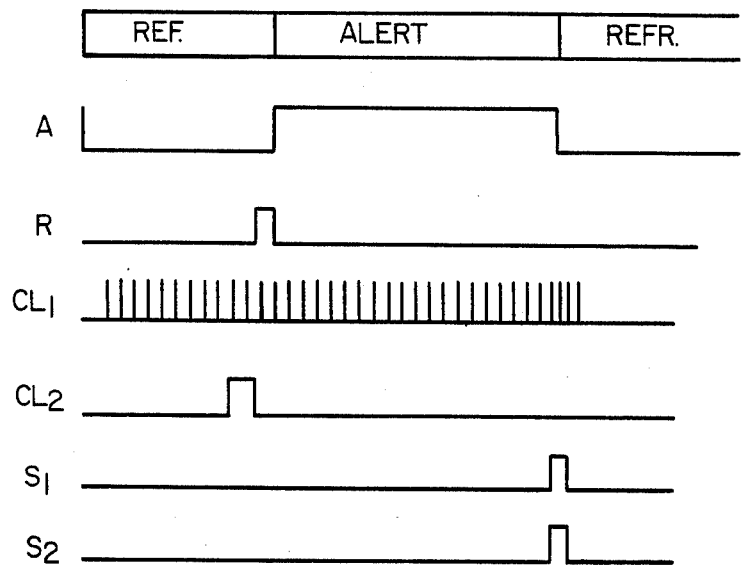
FIG. 5 is a timing diagram of the pulses during a paper refractory period and alert period.

Referring to FIG. 5, it is seen that signal A is high during the alert period and low during the refractory period. Signal R occurs prior to the end of the refractory period. Several clock signals (CL1 and CL2) are also shown. Outputs S1 and S2 from sense amplifiers 34, 36 are illustrated also.

Figure 6:
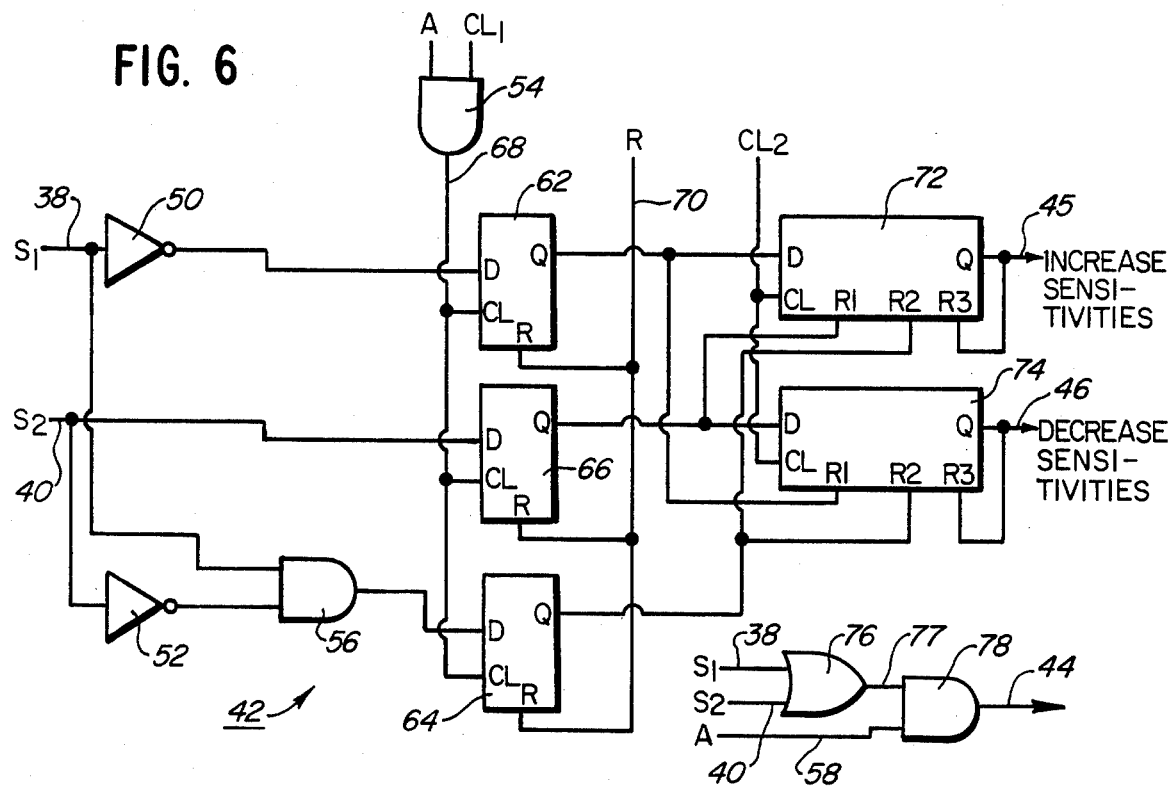
FIG. 6 is a logic diagram of a control system for controlling the automatic sensitivity adjustment of a cardiac pacer in accordance with the principles of the present invention.

Now referring to FIG. 6, controller 42 observes, during the alert period, outputs S1 and S2 on lines 38 and 40, respectively, from sense amplifiers 34 and 36, respectively. If S1 stays low, this indicates that the pacer has not sensed. If S2 goes high, this indicates that the sensitivity is potentially too high.

Controller 42 may require that either of these conditions occurs during several successive cycles, particularly the first situation in which S1 stays low. This is because lack of sensing can be caused either by too low a sensitivity or because no intrinsic cardiac rhythm was occurring to be sensed. A condition in which S2 goes high may be caused by noise that is not detected in the noise sensing circuitry and, therefore, the controller may observe several successive cycles. The number of cycles waited before sensitivities are changed may be externally programmed. A typical number which might be used is four, although this number may be varied.

More pacer-dependent patients will have fewer intrinsic beats and hence require a longer delay before readjusting sensitivity when S1 stays low. A condition in which S2 is high and S1 is low is assumed to never occur because sense amp 34 is always more sensitive than sense amp 36. This condition, if it does occur, indicates a malfunction. A specific design may detect this malfunction and initiate an alternative operation. The condition when S1 goes high and S2 stays low during the alert period is ideal and requires no readjustment of sensitivity.

Referring to the logic circuit of FIG. 6, line 38 is connected to an inverter 50 and line 40 is connected to an inverter 52. The output of inverter 52 is connected to an input of AND gate 56. Line 38 is connected to the other input of AND gate 56. Signal A which is high during the alert period and low during the refractory period and clock pulses CL1 are connected to AND gate 54.

The outputs of inverter 50 and AND gate 56 are connected to the data inputs of flip-flops 62 and 64, respectively. Line 40 is connected to the data input of flip-flop 66. The output of AND gate 54 is applied to the clock inputs of flip-flops 62, 64 and 66 via line 68 and the R signal which occurs prior to the end of the refractory period is applied to the reset inputs of flip-flops 62, 64 and 66 via line 70.

The Q output of flip-flop 62 is connected to the data input of shift register or counter 72 and the Q output of flip-flop 66 is connected to the data input of shift register or counter 74. The Q output of flip-flop 64 is connected to the R2 inputs of shift registers or counters 72 and 74. The Q output of flip-flop 66 is also connected to the R1 input of shift register or counter 72 and the Q output of flip-flop 62 is also connected to the R1 input of shift register or counter 74.

The sensed signal indicator portion of the controller 42 includes OR gate 76 which receives S1 and S2 as inputs and which outputs via line 77 to AND gate 78. AND gate 78 also has an input comprising line 58 carrying signal A (which is high during the alert period and low during the refractory period).

In the operation of the logic circuit of FIG. 6, inverter 50 generates $\overline{S1}$. This condition is clocked into flip-flop 62 by the output of AND gate 54, A.CL$_1$ clock pulses, which occur frequently during the alert period. This causes the Q output of flip-flop 62 to go high.

Condition S2 is clocked into flip-flop 66, causing the Q output of flip-flop 66 to go high.

The output of inverter 52 is $\overline{S2}$ and the output of AND gate 56 is S1.$\overline{S2}$. When this condition occurs, the Q output of flip-flop 64 goes high.

Thus, the Q output of flip-flop 62 indicates no sensing during the alert period, the Q output of flip-flop 66 indicates too high a sensitivity and the output of flip-flop 64 reflects ideal operation. All three flip-flops 62, 66 and 64 are reset by signal R, occurring every cycle.

The outputs of flip-flops 62 and 66 may alone be used to control sensitivity. However, a counting scheme which observes consistent operation for a number of cycles may be advantageous. To this end, shift registers or counters 72 and 74 are utilized. Either can count to any given independently programmable number from 0 to N. Whenever the Q output of counter 72 goes high, sensitivities are increased one step. Whenever the output of counter 74 goes high, sensitivities are decreased one step. These circuits are clocked by clock pulses CL2 once each cycle during the refractory period, prior to resetting flip-flops 62, 66 and 64.

Counter 72 is reset under any of three conditions: (1) flip-flop 66 goes high, (2) flip-flop 64 goes high or (3) counter 72 output has just gone high. Counter 74 is reset if either flip-flop 62 goes high, flip-flop 64 goes high, or the counter 74 output has just gone high. Counters 72 and 74 will have narrow pulse outputs if resetting is accomplished as in FIG. 6.

Although illustrative embodiments have been shown and described, it is to be understood that various modifications and substitutions may be made by those skilled in the art without departing from the novel spirit and scope of the present invention.

What is claimed is:

1. In a cardiac pacer including a pulse generator for providing pacing pulses and an electrical lead for connection to a chamber of the heart, the improvement comprising, in combination:
    a pair of separate sensing amplifiers for receiving the same polarity of a cardiac waveform;
    means for connecting said electrical lead to both of said separate sensing amplifiers so that both of said sensing amplifiers will receive the same polarity of the cardiac waveform simultaneously;
    one of said sensing amplifiers having a slightly lower threshold and thus a slightly higher sensitivity level than the other sensing amplifier; and
    means for adjusting the thresholds of the respective sensing amplifiers so that said one sensing amplifier will sense said cardiac waveform and said other sensing amplifier will not sense said cardiac waveform; said adjusting means comprises control circuit means coupled to the outputs of each of said sensing amplifiers and including feedback means from said control circuit means to each of said sensing amplifiers.

2. In a cardiac pacer as described in claim 1, in which said control circuit means comprises three flip-flops, the output of one of which is adapted for indicating that there is not sensing during the alert period, the output of a second of which is adapted for indicating that said other amplifier is too sensitive, and the third flip-flop is adapted for indicating ideal operation with said one sensing amplifier sensing said selected activity and said other sensing amplifier not sensing said selected activity.

3. In a cardiac pacer as described in claim 2, said control circuit further including a counter connected to the outputs of said flip-flops for providing an increase sensitivity signal and a counter connected to the outputs of said flip-flops for providing a decrease sensitivity signal.

4. A cardiac pacer which comprises:
    a pulse generator for providing pacing pulses;

an electrical lead the proximal end of which is connected to said pulse generator and the distal end of which is adapted for connection to a chamber of the heart;

a first sensing means for receiving a selected polarity of a cardiac waveform;

a second sensing means for receiving said selected polarity of the cardiac waveform;

means for coupling said electrical lead to said first and second sensing means so that said first and second sensing means will both receive the same polarity of the cardiac waveform;

means for providing said first sensing means with a first threshold;

means for providing said second sensing means with a second threshold;

feedback means coupled to the first and second sensing means for adjusting the first and second thresholds of the first and second sensing means so that said first sensing means will sense said cardiac waveform while said second sensing means will not sense said cardiac waveform.

5. A cardiac pacer as described in claim 4, in which said first and second sensing means comprise a pair of identical sensing amplifiers which are automatically and periodically adjusted to have different thresholds so that said first sensing amplifier will sense the selected activity of the heart chamber while the second sensing amplifier will not sense the selected activity of the heart chamber.

6. A cardiac pacer as described in claim 5, said feedback means including control means for adjusting the thresholds of said sense amplifiers, said control means operating to change the thresholds only after a predetermined number of cardiac events have occurred.

7. A cardiac pacer as described in claim 6, in which said control means comprises three flip-flops, the output of one of which is adapted for indicating that there is no sensing during the alert period, the output of a second of which is adapted for indicating that said second amplifier is too sensitive, and the third flip-flop is adapted for indicating ideal operation with said first sensing amplifier sensing said selected activity and said second sensing amplifier not sensing said selected activity.

8. A cardiac pacer as described in claim 7, said control means further including a counter connected to the outputs of said flip-flops for providing an increase sensitivity signal and a counter connected to the outputs of said flip-flops for providing a decrease sensitivity signal.

* * * * *